United States Patent [19]

DeTeresa

[11] Patent Number: 4,974,451
[45] Date of Patent: Dec. 4, 1990

[54] CONDUCTING FIBER COMPRESSION TESTER

[75] Inventor: Steven J. DeTeresa, Livermore, Calif.

[73] Assignee: The United States of America as represented by the United States Department of Energy, Washington, D.C.

[21] Appl. No.: 447,475

[22] Filed: Dec. 7, 1989

[51] Int. Cl.⁵ .............................................. G01N 3/08
[52] U.S. Cl. ...................................... 73/821; 324/701
[58] Field of Search ............... 73/818, 821; 324/65 R, 324/691, 693, 701, 713; 338/13

[56] References Cited

U.S. PATENT DOCUMENTS

| 3,084,300 | 4/1963 | Sanchez | 338/2 |
| 3,252,321 | 5/1966 | Pfann | 73/88.5 |
| 3,572,102 | 3/1971 | Baratta | 73/93 |
| 4,393,716 | 7/1983 | Clark et al. | 73/818 |

FOREIGN PATENT DOCUMENTS 1197774 7/1970 United Kingdom ............ 324/65 R

Primary Examiner—Jerry W. Myracle
Attorney, Agent, or Firm—Michael B. K. Lee; L. E. Carnahan; William R. Moser

[57] ABSTRACT

The invention measures the resistance across a conductive fiber attached to a substrate place under a compressive load to determine the amount of compression needed to cause the fiber to fail.

20 Claims, 3 Drawing Sheets

CONDUCTING FIBER COMPRESSION TESTER

The United States Government has rights in this invention pursuant to Contract No. W-7405-ENG-48 between the U.S. Department of Energy and the University of California, for the operation of Lawrence Livermore National Laboratory.

BACKGROUND OF THE INVENTION

The invention relates to an improved means for determining the ultimate compressive properties, the compression required to cause fiber failure, of carbon, graphite, and other conducting fibers which may be used in advanced composites.

Previous methods and apparatus for determining the ultimate compressive properties of conducting fibers used in advanced composites all suffer from one or more deficiencies. The elastica loop test, as described by W. R. Jones and J. W. Johnson in *Carbon* Volume 9, pg. 645 (1971), is simply a bending test for a single fiber that provides a value of strain to failure. The failure from such a test may be either compressive or tensile, and material nonlinearity can contribute to errors in the measured failure strain. Furthermore, tedious measurements of the loop geometry are required to determine the strain in the fiber at the failure point. A more recently developed tensile recoil test, as described by S. R. Allen in the Journal of Material Science, Volume 22 (3) starting at page 853 (1987), is based on compressive stresses that are generated during recoil of a fiber after tensile fracture. Although this test can potentially yield values of fiber compressive strength, it is only applicable to fibers exhibiting tensile strength greater than compressive strength. Furthermore, the rate of deformation in the recoil test is both extremely high and uncontrollable and fiber bending during recoil may result in premature failure and anomalously low values of compressive strength. These problems encountered with this test are further described by C. S. Wang, S. J. Bai, and B. P. Rice in the Proceedings of the ACS Division of Polymeric Materials: Science and Engineering, Volume 61, beginning at page 550 (1989). Attempts have been made to calculate fiber compressive strengths using strengths of composites containing a multiplicity of fibers in a matrix binder. Unfortunately, it is extremely difficult to determine the mode of failure in a composite and to determine the effects of matrix properties, fiber-matrix adhesion and imperfections on the measured composite strength. Additionally, composite strengths measured using different test methods for one material can vary widely. Consequently, very little information can be gleaned from composite tests alone.

H. M. Hawthorne and E. Teghtsoonian in The Journal of Material Science, Volume 10(1) beginning at page 41 (1975) describe a fiber compression test which involves compression of a fiber embedded in a transparent matrix. In this test, the strains in the matrix and the fiber are identical and can be easily measured on the surface of the matrix. Fiber failure must be detected by visual observation. The advantages of this test include uniform compression of the fiber, controllable deformation rates and results that are independent of material nonlinearity. Major drawbacks of this test are the unknown residual strains in the fiber resulting from shrinkage of the matrix during the embedding process and the tedious effort required to visualize fiber failure which can occur anywhere along the length of the embedded fiber.

SUMMARY OF THE INVENTION

It is an object of the invention to accurately measure the amount of compression needed to cause a conducting fiber to fail with such failure only caused by a compressive load.

It is another object of the invention to measure the amount of compression needed to cause a conducting fiber to fail which is independent of the fiber material's nonlinearity.

It is another object of the invention to measure the amount of compression needed to cause a conducting fiber to fail when the fiber's compressive strength is greater than its tensile strength.

It is another object of the invention to accurately measure the amount of compression needed to cause a conducting fiber to fail without measuring loop geometry.

It is another object of the invention to accurately measure the amount of compression required to cause a conducting fiber to fail without requiring visual inspection of the fiber.

These and other objects of the invention will become readily apparent to those skilled in the art from the following description and accompanying drawings.

The invention measures piezoresistive behavior across a conducting fiber attached to a substrate placed under a compressive load to measure the amount of compression needed to cause the fiber to fail.

It is well known that carbon, graphite and other conducting fibers used for reinforcement in advanced composite materials exhibit piezoresistive behavior, such that the electrical resistance of the fiber changes when it is stressed or strained. Typically, the fiber resistance increases when stretched and decreases when compressed. This property is exploited in the inventive apparatus. By monitoring the piezoresistive behavior of a fiber in compression, the inventive apparatus provides (1) indication of whether or not the fiber is truly in compression and (2) indication of compressive fracture and strain at which fracture occurred. The latter is typically manifested as an abrupt increase in electrical resistance due to the concomitant disruption of the fiber structure and its ability to conduct electrical current.

DETAILED DESCRIPTION OF THE INVENTION

Figure 1:
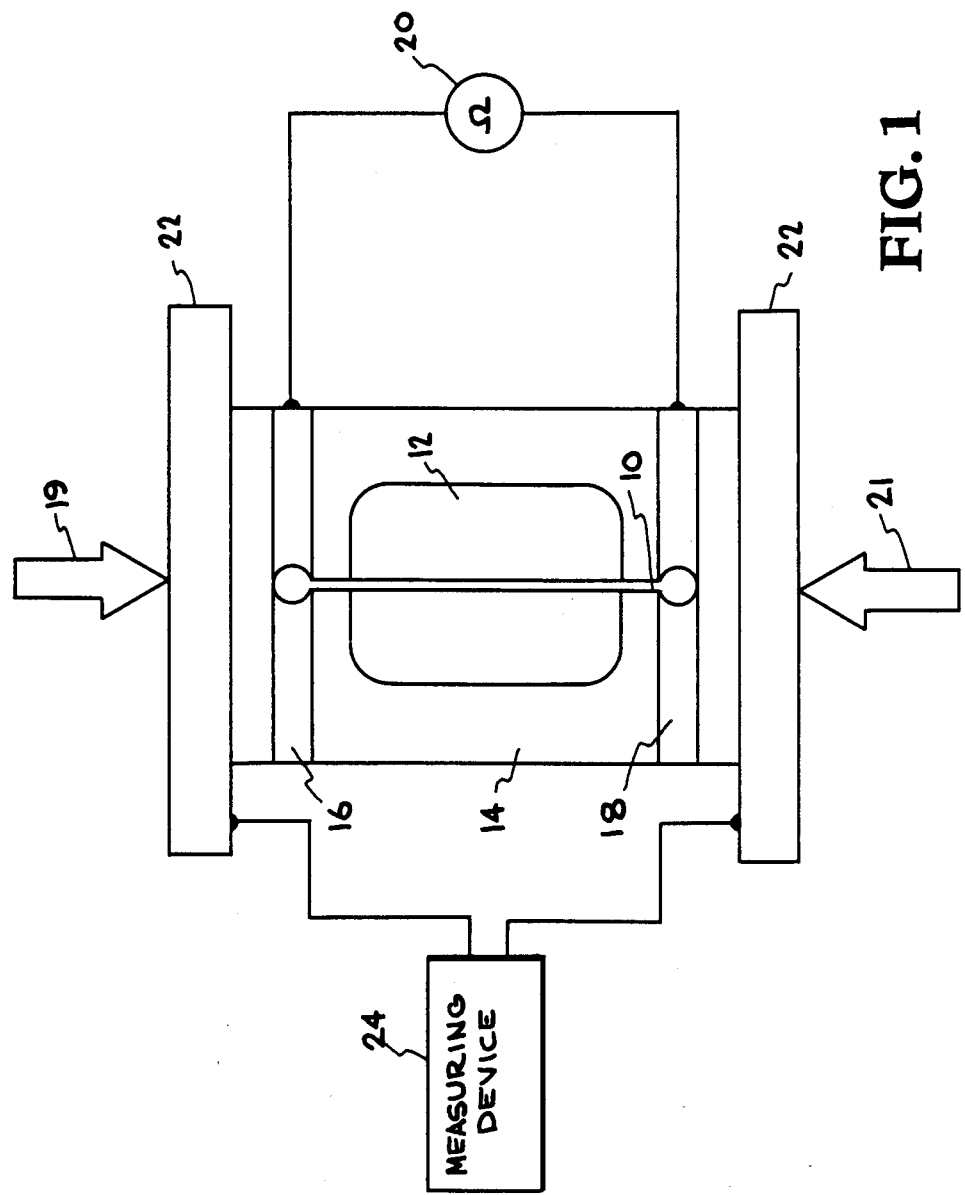
FIG. 1 is an illustration of a preferred embodiment of the invention, which is an apparatus which measures ultimate compressive strain.

FIG. 1 shows an apparatus which may be used to practice the invention. The embodiment of the inventive apparatus illustrated in FIG. 1 was used to test a conducting fiber 10, which was linear and has a first end and a second end and a center region between the first end and second end. An adhesive 12 was used to bond the center region of the conducting fiber 10 to a substrate 14, which has a first end and a second end. A first metal strip 16 was mechanically attached to the substrate 14 as shown. The first end of the conducting fiber 10 was mechanically and electrically attached to the first metal strip 16, wherein the place of attachment between the first metal strip 16 and the first end of the conducting fiber 10 lies between the first end of the substrate 14 and the center region of the conducting fiber 10. A second metal strip 18 was mechanically attached to the substrate 14 as shown. The second end of the conducting fiber 10 was mechanically and electrically attached to the second metal strip 18, wherein the place of attachment between the second metal strip 18 and the second end of the conducting fiber 10 was located between the second end of the substrate 14 and the center region of the conducting fiber 10. A device 20 for measuring resistance was electrically connected between the first metal strip 16 and the second metal strip 18. A compression device 22 for deforming the substrate and bonded fiber was placed across the first end and the second end of the substrate. The embodiment illustrated in FIG. 1 also comprised a device 24 for measuring the deformation or compression of the substrate.

The device measures ultimate compressive strain by compressing the first and second ends of the substrate together, while measuring the displacements of the substrates ends and the resistance through the conducting fiber. The directions of the compressive forces are illustrated by arrows 19 and 21. The value of displacement at which the fiber resistance increases abruptly due to fiber failure was recorded. The ultimate fiber compressive strain was calculated from this displacement after correcting for residual strain.

In the preferred embodiment, the substrate 14 was in the shape of a rectangular prism. The substrate 14 preferably is of a geometry that yields uniform compression of the fiber when the substrate is deformed. A circular cylinder is another suggested shape for the substrate. The substrate 14 should be made of a material that has adequate rigidity (tensile modulus greater than or equal to 1 Giga Pascal (GPa)), failure strain greater than that of the fiber, and electrical insulator properties. It may also be desirable that the substrate be transparent to allow visual observation of certain aspects of the test. Some examples of materials that may be used for the substrate include thermosetting polymers such as epoxies, phenolics, and polyesters and thermoplastic polymers such as polycarbonates, acrylics, and polyesters.

The adhesive 12 used to bond the carbon fiber 10 to the surface of the substrate 14 transmits compressive strain from the substrate surface to the center region of the fiber 10 and supports the center region of the fiber 10 against buckling. Mounting the fiber 10 on the surface of the substrate 14 offers an advantage over embedding fibers in a matrix in that any shrinkage of the adhesive coating during curing or hardening can only occur perpendicular to the surface of the substrate, since the rigid substrate restrains the adhesive coating from shrinking along the direction of the fiber axis. Therefore, minimal or no residual strains are generated in the fiber due to the application of the adhesive coating. If an elevated temperature is required to completely cure or harden the adhesive coating, then a residual strain in the fiber along its axis will be generated during cooldown to test temperature due to thermal expansion mismatch between the fiber 10 and the substrate 14. The magnitude of this residual strain can be calculated using:

$$e_r = (a_s - a_f)(T_t - T_c)$$

where:

$e_r$ = residual strain in the fiber $a_s$ = thermal expansion coefficient of the substrate $a_f$ = thermal expansion coefficient of the fiber along its length $T_t$ = test temperature $T_c$ = cure temperature This residual strain is added to the measured strain on the substrate at fracture to determine the compressive strain at which the conducting fiber fails.

The adhesive 12 should be a material that has good adhesion to both the fiber 10 and the substrate 14, adequate rigidity (tensile modulus greater than or equal to 1 GPa), failure strain greater than that of the fiber 10, cure or hardening temperature below the softening point of the substrate, and electrical insulating properties. In the preferred embodiment the adhesive is also transparent to allow visual observation of the fiber 10. Examples of adhesives that may be used include thermosetting polymers such as epoxies, phenolics, and polyesters and thermoplastic polymers such as acrylics.

The ends of the conducting fiber 10 are mechanically and electrically attached to the first and second metal strips 16, 18. The mechanical and electrical attaching may use a conductive adhesive, which could be a conductive paint used as an adhesive. The conductive adhesive used to establish electrical contact between the fiber ends and the metal strips can be composed of graphite or silver particles in a solvent suspension or an adhesive.

In the preferred embodiment, the metal strips 16 and 18 are copper and are mechanically or adhesively fixed to the substrate. If an adhesive is used, a soft compliant adhesive is preferable since this type will transmit little or no strain to the metal strips thereby guaranteeing that the fiber 10 is deformed exclusively in the center region of the fiber. In the preferred embodiment, the metal strips 16 are linear, but the metal strips may be of other shapes and sizes.

The device 20 for measuring resistance can be an ohm meter or a Wheatstone bridge or any other device used for measuring resistance. The electrical leads of the measuring device are attached between the metal strips. This may be done by welding, soldering or by using other types of electrical connections.

The compression device 22 can be any device capable of a controlled squeezing motion between two parallel surfaces which would be the first and the second ends of the substrate. Several devices can be used for this purpose such as commercial materials testing machines, hydraulic and mechanical presses, and screw vises.

The device 24 for measuring deformation or compression of the substrate could be any device that measures the displacement of the parallel surfaces of the compression device or one that measures the displacement of the substrate surface directly. Commercial extensometers or linear variable differential transformers (LVDT) or metal foil strain gauges are some of the devices that could be used for the deformation measuring device 24.

EXAMPLE

Figure 2:
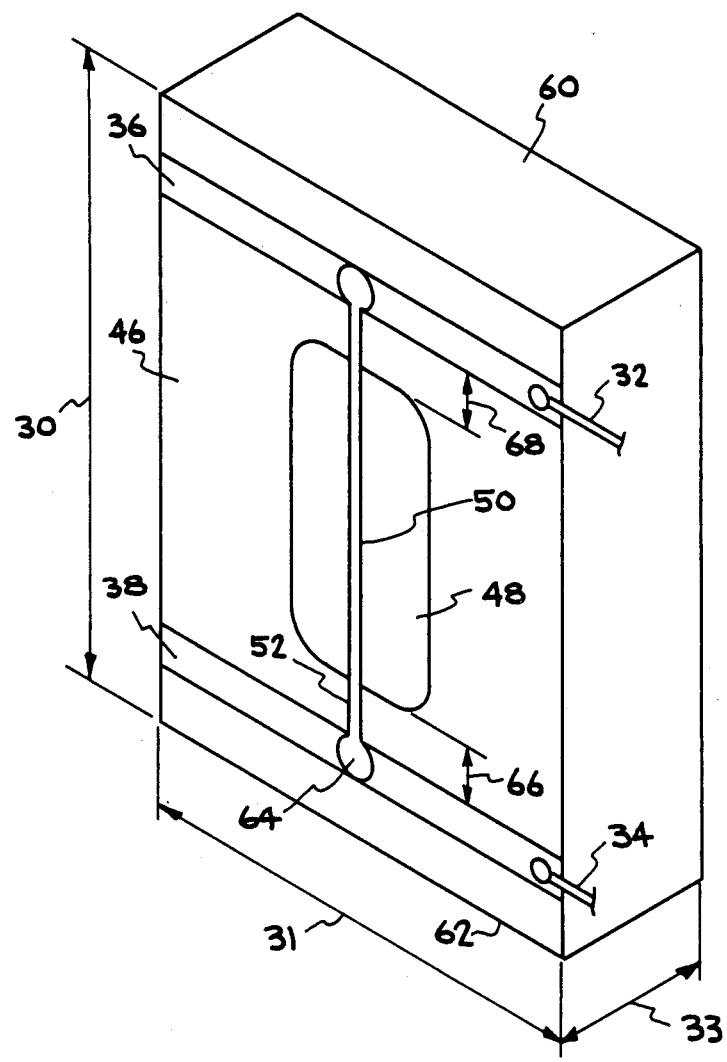
FIG. 2 is a detailed view of the substrate used in a specific example.
Figure 3:
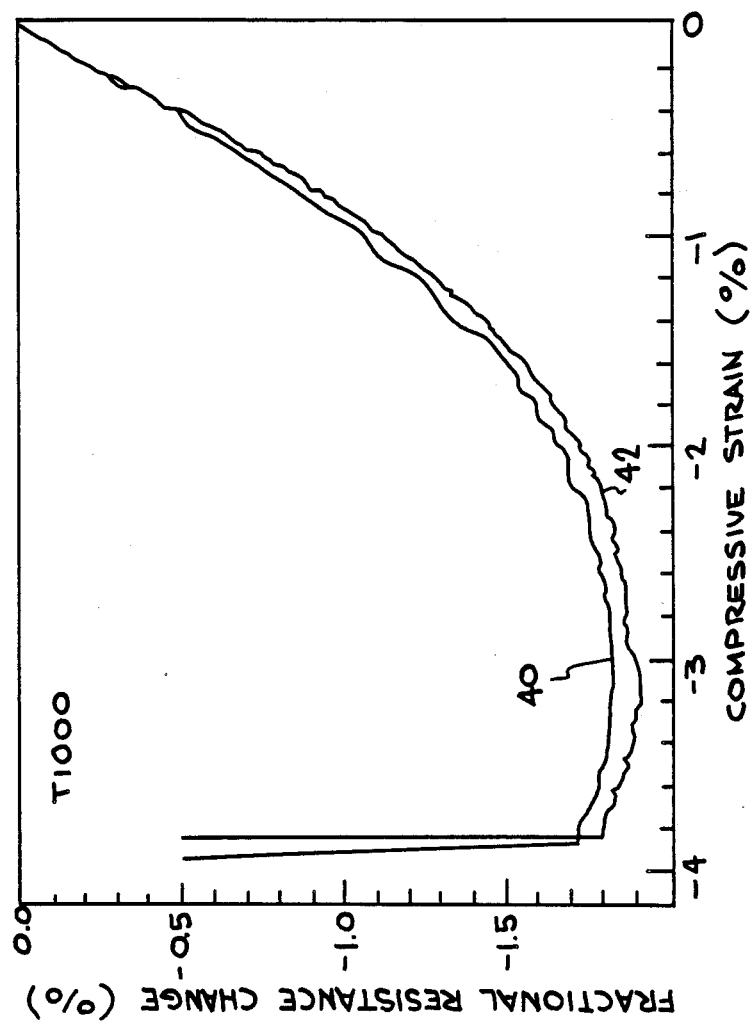
FIG. 3 is a plot of fractional resistance change verses compressive strain in two specific examples.

FIGS. 2 and 3 relate to specific examples of the use of the invention. Substrates of poly(carbonate of bisphenol A) (PC) and poly(methyl methacrylate) (PMMA) were machined to the shape of rectangular prisms as shown in FIG. 2. The height 30 of the prisms was 1 inch, with the width 31 and thickness 33 being ½ inch. After cleaning the surfaces of the substrate, ⅛ inch wide strips 36 and 38 of adhesive-backed copper (CHR Industries, C661)

were fixed to a first outer surface 46 of each specimen as shown in FIG. 2. Single filaments of Torayca T1000 graphite fiber were removed from a 12K tow that had previously been washed free of sizing. A single filament (fiber) 52 was aligned under slight tension across the first outer surface 46 of each substrate and fixed at either end to the copper strips with a colloidal graphite paint (Structure Probe, Inc.) 64. After allowing sufficient drying time for the graphite paint, the center region 50 of each filament 52 was bonded to the surface of the substrate by applying an adhesive coating 48. Filaments 52 were bonded to PC substrates with an epoxy coating (Dow DER 332 epoxy resin with Texaco Jeffamine T-403 amine curing agent). The epoxy coating was allowed to cure 1 day at ambient temperature and post-cure 3 days at 50° C. Filaments were bonded to PMMA substrates with a UV curable rigid acrylic coating (Dymax Light Weld 186). Regions 66 and 68 between the copper strips 36 and 38 and the adhesive 48 are left unbound to allow the fiber 52 to buckle at those regions. Both the epoxy and acrylic coatings are transparent and surpass the minimum requirements for rigidity (tensile modulus greater than 1 GPa). All specimens were fitted with lead wires that were soldered to each copper strip at solder points 32 and 34. Specimens were compressed using an Instron test machine equipped with an extensometer to measure the displacement of the loading surfaces. The compressive load is applied to the first end 60 and the second end 62 of the substrate. The first end 60 of the substrate is a second outer surface of the substrate, which is substantially perpendicular to the first outer surface 46 of the substrate. The second end 62 of the substrate is a third outer surface of the substrate, which is substantially perpendicular to the first outer surface 46 of the substrate and substantially parallel to the first end 60 of the substrate. The filament resistance was monitored by incorporating the filament as the active arm of a Wheatstone bridge and recording the voltage drop across this bridge.

The recorded outputs from a PMMA/acrylic-coated specimen 40 and a PC/epoxy-coated specimen 42 are shown in FIG. 3. The specimens exhibited near identical piezoresistive behavior. Furthermore, both specimens exhibited an abrupt increase in resistance, corresponding to filament compressive failure, at a compressive strain of −3.8%. Failure of the filament in both specimens was in a shear mode.

The foregoing description of a preferred embodiment of the invention has been presented for purposes of illustration and description. It is not intended to be exhaustive or to limit the invention to the precise form disclosed, and obviously many modifications and variations are possible in light of the above teaching. The embodiment was chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

I claim:

1. An apparatus for measuring the ultimate compressive properties of a conducting fiber with a first end and a second end and a center region between the first end and second end, comprising:
    a substrate with a first outer surface, a first end and a second end with the first outer surface extending between the first end and the second end of the substrate;
    means for mechanically attaching the center region of the conducting fiber to the first outer surface of the substrate;
    means for measuring the electrical resistance across the conducting fiber; and
    means for applying a compressive load on the first end and the second end of the substrate.

2. An apparatus as claimed in claim 1, further comprising, a means for measuring the compressive strain on the substrate.

3. An apparatus as claimed in claim 2, wherein the substrate has a failure strain greater than that of the conductive fiber.

4. An apparatus as claimed in claim 3, wherein the means for measuring the electrical resistance across the conducting fiber, comprises a resistance meter with a first lead electrically connected to the first end of the conducting fiber and a second lead electrically connected to the second end of the conducting fiber.

5. An apparatus as claimed in claim 4, wherein the means for measuring the electrical resistance across the conducting fiber, further comprises;
    a first conducting strip mechanically attached to the first outer surface of the substrate and electrically attached between the first lead of the resistance meter and the first end of the conducting fiber; and
    a second conducting strip mechanically attached to the first outer surface of the substrate and electrically attached between the second lead of the resistance meter and the second end of the conducting fiber.

6. An apparatus as claimed in claim 5, wherein the first end of the substrate is a second outer surface of the substrate and the second end of the substrate is a third outer surface of the substrate which is substantially parallel to the first end of the substrate and wherein the first outer surface of the substrate is substantially perpendicular to the first and second ends of the substrate.

7. An apparatus as claimed in claim 6, wherein the means for attaching part of the center region of the conducting fiber to the substrate is an adhesive which has a tensile modulus greater than or equal to 1 Giga Pascal and a failure strain greater than that of the conductive fiber and is an electrical insulator.

8. An apparatus as claimed in claim 7, wherein the substrate has a tensile modulus greater than or equal to 1 Giga Pascal, and wherein the substrate is an electrical insulator.

9. An apparatus as claimed in claim 8, wherein the adhesive and the substrate are transparent.

10. An apparatus as claimed in claim 9, further comprising a first conducting adhesive electrically connected between the first end of the conducting fiber and the first conducting strip and a second conducting adhesive electrically connected between the second end of the conducting fiber and the second conducting strip.

11. An apparatus as claimed in claim 10, further comprising;
    a first region between the center region of the fiber and the first end of the fiber, which is not bound to the substrate or the first conducting strip where the fiber may buckle under stress; and
    a second region between the center region of the fiber and the second end of the fiber, which is not bound to the substrate or the first conducting strip where the fiber may buckle.

12. A method for measuring the ultimate compressive properties of a conducting fiber with a first end and a second end and a center region between the first end and the second end, comprising the steps of:

attaching part of the center region of the conducting fiber to a first outer surface of a substrate, wherein the substrate has a first end and a second end and wherein the first outer surface extends between the first end and the second end of the substrate;

placing a compressive load on the first end and the second end of the substrate; and measuring the resistance across the conducting fiber.

13. A method as claimed in claim 12, further comprising the step of measuring the compressive strain on the substrate.

14. A method as claimed in claim 13, wherein the compressive load is increased until the resistance across the conducting fiber abruptly increases.

15. A method as claimed in claim 14, wherein the step of attaching part of the center region of the conducting fiber to the outer surface of the substrate comprises the step of applying an insulating adhesive to part of the first outer surface of the substrate and part of the center region of the conducting fiber.

16. A method as claimed in claim 15, wherein the step of measuring the resistance across the conducting fiber, comprises the steps of:

mechanically attaching a first conducting strip to the substrate;

mechanically attaching a second conducting strip to the substrate;

mechanically and electrically attaching the first end of the conducting fiber to the first conducting strip;

mechanically and electrically attaching the second end of the conducting fiber to the second conducting strip;

electrically connecting a first lead of a resistance measuring device to the first conducting strip; and electrically connecting a second lead of a resistance measuring device to the second conducting strip.

17. A method as claimed in claim 16, wherein the substrate has a tensile modulus greater than or equal to 1 Giga Pascal and a failure strain greater than that of the fiber.

18. A method as claimed in claim 17, wherein the insulating adhesive has a tensile modulus greater than or equal to 1 Giga Pascal and a failure strain greater than that of the fiber.

19. A method as claimed in claim 18, wherein the substrate and the insulating adhesive are transparent.

20. A method as claimed in claim 19, wherein the first end of the substrate is a second outer surface which is substantially parallel to the second end of the substrate which is a third outer surface of the substrate and wherein the first end of the substrate and the second end of the substrate are substantially perpendicular to the first outer surface of the substrate.

* * * * *